(12) United States Patent
Kim et al.

(10) Patent No.: US 8,173,756 B2
(45) Date of Patent: May 8, 2012

(54) PHOTOPOLYMERIZABLE MONOMERS HAVING EPOXIDE AND UNSATURATED DOUBLE BONDS AND THEIR COMPOSITION

(75) Inventors: Eunkyoung Kim, Seoul (KR); Jeonghun Kim, Seoul (KR); Hyunjin Oh, Gwangju-si (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 557 days.

(21) Appl. No.: 12/337,041

(22) Filed: Dec. 17, 2008

(65) Prior Publication Data

US 2009/0163683 A1  Jun. 25, 2009

(30) Foreign Application Priority Data

Dec. 24, 2007  (KR) .......... 10-2007-0136850

(51) Int. Cl.
*C08F 12/30*  (2006.01)
(52) U.S. Cl. ........ 526/286; 526/261; 526/266; 526/273; 526/288
(58) Field of Classification Search .......... 526/286, 526/261, 266, 273, 288
See application file for complete search history.

(56) References Cited

U.S. PATENT DOCUMENTS

| | | |
|---|---|---|
| 4,842,968 A | 6/1989 | Kojima et al. |
| 5,887,135 A | 3/1999 | Dahlen et al. |
| 6,221,536 B1 | 4/2001 | Dhar et al. |
| 6,268,089 B1 | 7/2001 | Chandross et al. |

FOREIGN PATENT DOCUMENTS

| | | | |
|---|---|---|---|
| JP | 2001075275 | * | 3/2001 |
| KR | 1989-0010615 (A) | | 8/1989 |
| KR | 1991-0001467 (A) | | 1/1991 |
| KR | 1993-0004161 (B1) | | 5/1993 |
| KR | 1996-0006168 (B1) | | 5/1996 |
| KR | 0132430 (B1) | | 4/1998 |
| KR | 10-0196589 (B1) | | 6/1999 |

OTHER PUBLICATIONS

Waldman, D.A. et al.: "Cationic Ring-Opening. Photopolymerization Methods for Volume Hologram Recording", *SPIE*, vol. 2689, pp. 127-140, 1996.
Takata, Toshikazu et al.: "Recent Advances in the Development of Expanding Monomers: Synthesis, Polymerization and Volume Change", *Prog. Polym. Sci.*, vol. 18, 1993, pp. 839-870.
Bolin, Carsten et al.: "Synthesis and Photoinitiated Cationic Polymerization of 2-Methylene-7-phenyl-1,4,6,9-tetraoxaspiro[4.4]nonane", *Macromolecules*, 1996, 29 (9), pp. 3111-3116.

* cited by examiner

*Primary Examiner* — Edward Cain
(74) *Attorney, Agent, or Firm* — Frommer Lawrence & Haug LLP; Ronald S. Santucci

(57) ABSTRACT

Provided are a novel photopolymerizable monomer having at least one unsaturated double bond and epoxide, and a photocurable composition comprising the photopolymerizable monomer and an initiator, which is polymerizable with good efficiency using light and/or heat, provides reduced shrinkage, and has superior mechanical strength including adhesion and transparency.

5 Claims, 1 Drawing Sheet

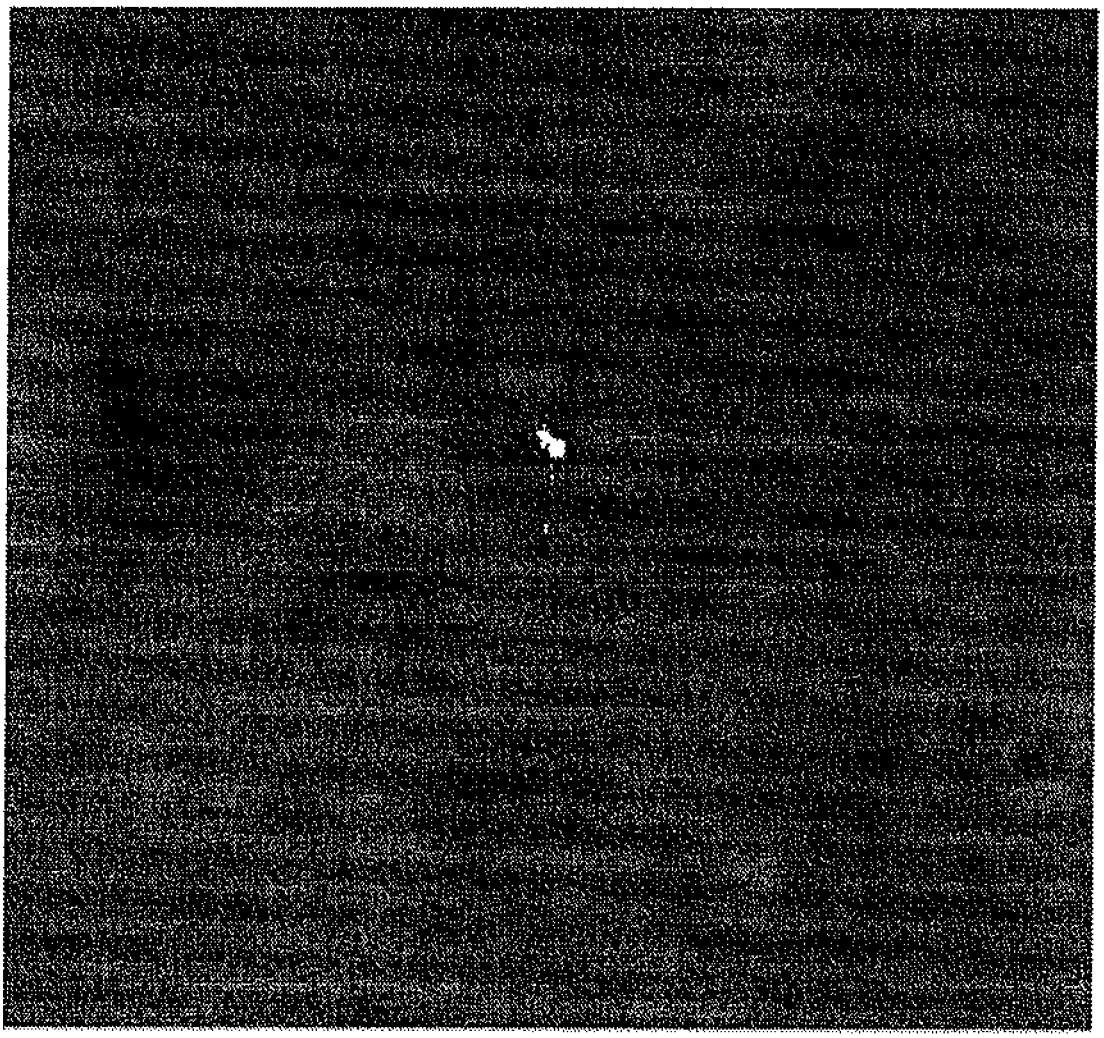

PHOTOPOLYMERIZABLE MONOMERS HAVING EPOXIDE AND UNSATURATED DOUBLE BONDS AND THEIR COMPOSITION

CROSS-REFERENCE TO RELATED APPLICATION

This applications claims under 35 U.S.C. §119(a) the benefit of Korean Patent Application No. 10-2007-0136850 filed, Dec. 24, 2007, the entire contents of which are incorporated herein by reference.

BACKGROUND (a) Technical Field

The present invention relates to a novel photopolymerizable monomer having at least one unsaturated double bond and epoxide, and a photocurable composition comprising the photopolymerizable monomer and an initiator.

(b) Background Art

Monomers having unsaturated double bonds are easily polymerizable with light or heat, and are highly sensitive to light.

Photocurable compositions are cured by light to form solid or highly viscous films. Therefore, they are used in the manufacture of protective films, surface coatings, electrolyte permeable/non-permeable films, functional films for electronic devices, recording films, and the like.

In general, a photopolymer, wherein the degree of polymerization becomes different depending on the intensity of light irradiation, comprises an acryl or epoxy monomer, an initiator and a polymer binder. Acryl based films are widely applicable, but tend to experience severe shrinkage upon curing by light or heat. In contrast, epoxy based films experience less shrinkage, but have low reactivity. Various photopolymerizable compositions have been developed to solve this problem.

For instance, Korean Patent Publication No. 1992-4550 discloses a photopolymerizable composition comprising a) a polymerizable binder, b) a free radical polymerizable compound having at least one terminal ethylenic double bond, and c) an N-heterocyclic compound, a thioxanthone derivative and a dialkylamino compound as photoinitiator.

And, Korean Patent Publication Nos. 1991-17382, 1991-1467, 1990-3685, 1990-3685, 1989-10615 and 1988-11262, and US Patent Application No. 08/698,142 disclose photopolymerizable compositions comprising acrylates or alkacrylates of polyalcohols as main components together with liquid monomers such as free radical polymerizable acrylate ester.

However, these compositions are accompanied by the problem that shrinkage occurs during the polymerization of the monomers, thereby causing trouble in deciphering the recorded information.

To solve these problems, Waldman et al. used cationic epoxy polymerization to form holograms, and, because epoxy polymerization involves opening of the epoxide monomer rings, the polymerization exhibits about half as much shrinkage as acrylate polymerizations [Waldman et al., "Cationic Ring-Opening Photopolymerization Methods for Volume Hologram Recording", SPIE vol. 2689, 1996, 127]. It has further been proposed that spiro-orthoesters and spiro-orthocarbonates, so-called expanding monomers, be added to epoxy polymerization systems [Expanding Monomers: Synthesis, Characterization, and Applications (R. K. Sadhir and R. M. Luck, eds., 1992) 1-25, 237-260; T. Takata and T. Endo, "Recent Advances in the Development of Expanding Monomers: Synthesis, Polymerization and Volume Change", *Prog. Polym. Sci.*, Vol. 18, 1993, 839-870]. Such spiro compounds have been reported to exhibit relatively small shrinkage, or even expansion, upon polymerization. And, U.S. Pat. No. 6,221,536 proposes adding a specific spiro compound as expansion agent in order to compensate for the polymerization-induced shrinkage.

However, the shrinkage compensating ability of the spiro compound is not so great because it is caused, at least in part, by a phase change. Also, the rates of ring-opening and accompanying fragmentation side reactions are difficult to tune [C. Bolin et al., "Synthesis and Photoinitiated Cationic Polymerization of 2-methylene-7-phenyl-1,4,6,9-tetraoxaspiro-[4,4] nonane," *Macromolecules*, Vol. 29, 1996, 3111-3116].

U.S. Pat. No. 4,842,968 discloses a hologram recording medium comprising a photoimaging material inside a porous glass material. This requires the process of removing the non-exposed region after irradiation of light, which may be accompanied by such problems as diffusion of solvent, unwanted chemical reaction, difficulty of removing unreacted monomers, and so forth.

U.S. Pat. No. 6,268,089 discloses a photorecording medium comprising a hybrid inorganic-organic matrix comprising a metallic element, e.g., silicon, titanium, germanium, zirconium, vanadium and aluminum, suitable for use in holographic storage systems. According to the process for holography of the invention, the photopolymerization of the precursor of the hybrid inorganic-organic matrix and the photochemical reaction of monomers by which holographic recording is carried out are independent of each other. As a result, the process of removing unreacted monomers can be eliminated, and improved thermal, mechanical and chemical stability are obtained through the combination of an oligomer and an oxide.

However, this method has the problem that the efficiency of photorecording may decrease as the photocurable monomers are polymerized during the polymerization of the hybrid inorganic-organic precursor (thermal curing).

The information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with the prior art, and it is an object of the present invention to provide a novel photopolymerizable monomer offering superior photopolymerization efficiency with good curing reactivity and less shrinkage, and a photocurable composition comprising the photopolymerizable monomer.

In one aspect, the present invention provides a photopolymerizable monomer of the following formula (1):

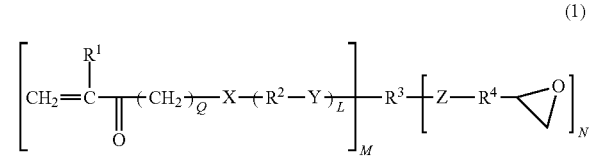

wherein
R$^1$ is H or CH$_3$;
R$^2$ is C$_1$-C$_{20}$ alkylene;
R$^3$ is C$_1$-C$_{20}$ alkyl, C$_1$-C$_{20}$ alkyleneoxy, or an aromatic ring, the aromatic ring being

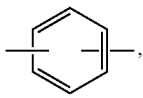

substituted

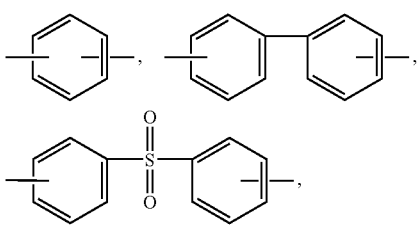

bisphenol alkylene, bisphenol ether, bisphenol S, or

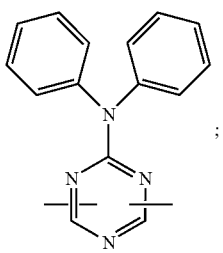

R$^4$ is C$_1$-C$_{20}$ alkylene or C$_2$-C$_{20}$ alkyleneoxyalkyl;
X is O or S;
Y and Z are independently O, S, O—C=O or S—C=O;
L is 0 or an integer of 1 to 30;
M and N are independently an integer of 1 to 3; and
q is 0 or an integer of 1 to 30.

In another aspect, the present invention provides a photocurable composition comprising 1 to 99.99 weight % of a photopolymerizable monomer of the formula (1) and 0.01 to 99 weight % of an initiator.

In still another aspect, the present invention provides a photopolymer obtained by polymerizing the photocurable composition.

The novel photopolymerizable monomer having unsaturated double bond and epoxide according to the present invention is polymerizable by heat or light with good photopolymerization efficiency. The photopolymer prepared from the photopolymerizable monomer can be prepared into a transparent film having superior mechanical strength and, thus, is applicable as substrate protective film, antireflective film, high-integrated pattern and imaging material in electric and electronic fields, including displays, electronic devices, photorecording systems, etc., and is also applicable to drug delivery systems in the medical field.

The above features and advantages of the present invention will be apparent from or are se forth in more detail in the accompanying drawing, which is incorporated in and forms a part of this specification, and the following Detailed Description section, which together serve to explain by way of example of the principles of the present invention.

BRIEF DESCRIPTION OF THE DRAWINGS

The above and other features of the present invention will now be described in detail with reference to certain exemplary embodiments thereof illustrated by the accompanying drawing which is given hereinbelow by way of illustration only, and thus is not limitative of the present invention:

FIG. 1 is a photograph showing the grating pattern of the photopolymer prepared in Example 4 obtained by exposure to laser radiation.

DETAILED DESCRIPTION

Reference will now be made in detail to the preferred embodiments of the present invention. The embodiments are described below so as to explain the present invention.

The present invention is characterized by a photopolymerizable monomer having at least one unsaturated double bond and epoxide, which has the following formula (1):

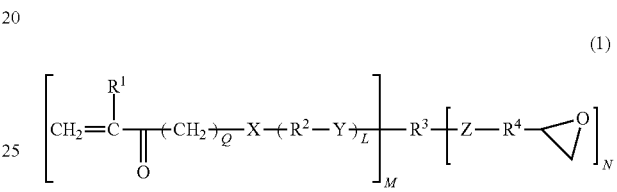

(1)

wherein
R$^1$ is H or CH$_3$;
R$^2$ is C$_1$-C$_{20}$ alkylene, preferably C$_1$-C$_{10}$ alkylene, more preferably C$_1$-C$_5$ alkylene;
R$^3$ is C$_1$-C$_{20}$ alkyl, C$_1$-C$_{20}$ alkyleneoxy, or an aromatic ring, the aromatic ring being

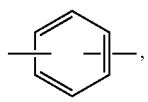

substituted

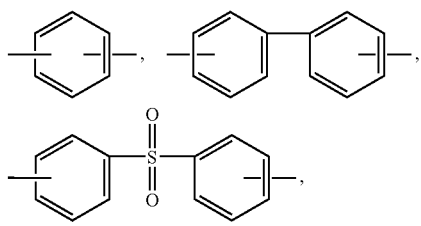

bisphenol alkylene, bisphenol ether, bisphenol S, or

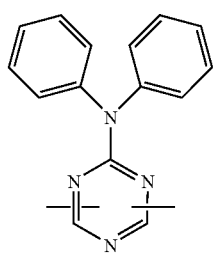

$R^4$ is $C_1$-$C_{20}$ alkylene or $C_2$-$C_{20}$ alkyleneoxyalkyl, preferably $C_1$-$C_{10}$ alkylene or $C_2$-$C_{10}$ alkyleneoxyalkyl, more preferably $C_1$-$C_5$ alkylene or $C_2$-$C_6$ alkyleneoxyalkyl;

X is O or S;

Y and Z are independently O, S, O—C=O or S—C=O;

L is 0 or an integer of 1 to 30, preferably 0 or an integer of 1 to 10, more preferably 0, 1 or 2;

M and N are independently an integer of 1 to 3, preferably 1 or 2; and q is 0 or an integer of 1 to 30, preferably 0 or an integer of 1 to 10, more preferably 0, 1 or 2.

Specific examples of the photopolymerizable monomer having the formula (1) are as follows:

Compound 1-1

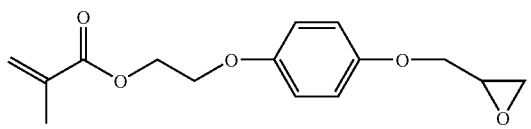

Compound 1-2

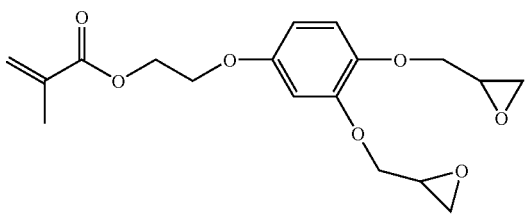

Compound 1-3

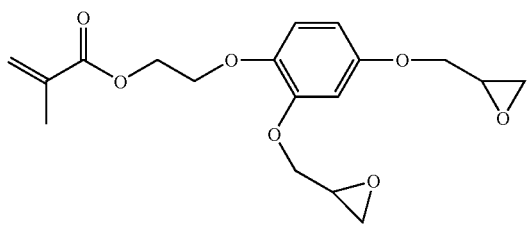

Compound 1-4

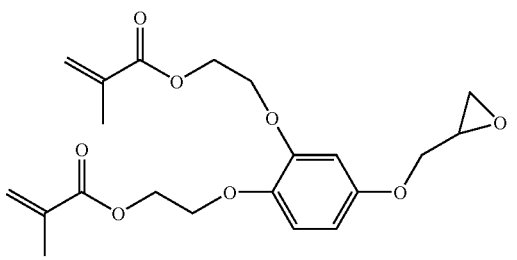

Compound 1-5

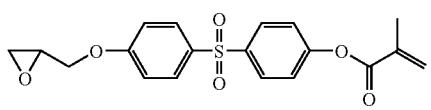

Compound 1-6

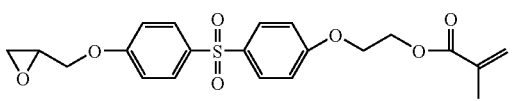

Compound 1-7

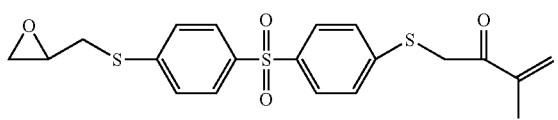

Compound 1-8

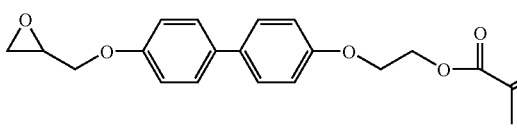

Compound 1-9

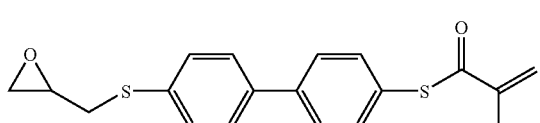

Compound 1-10

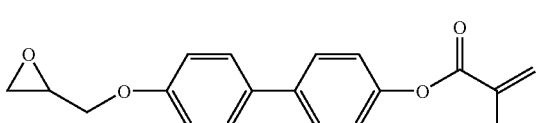

Compound 1-11

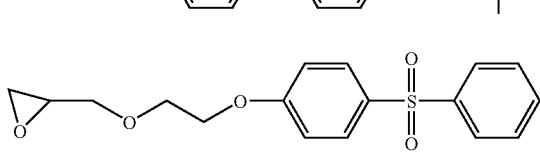

Compound 1-12

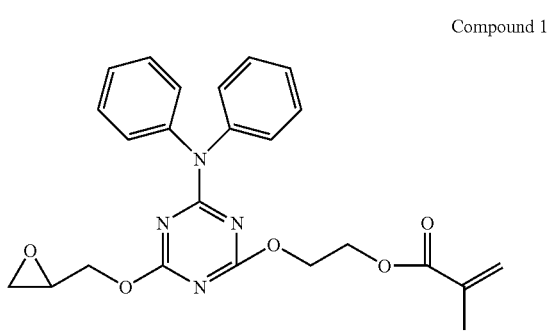

Compound 1-13

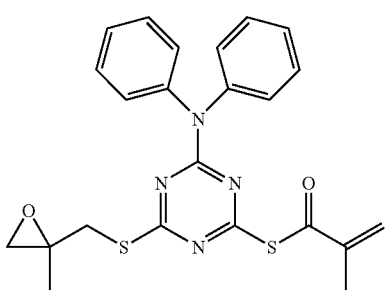

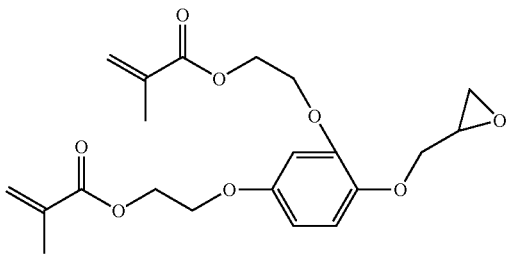

Compound 1-14

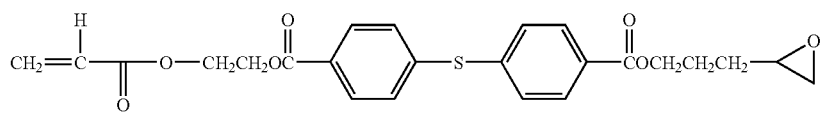

Compound 1-15

The compound of the formula (1) may be prepared by the method commonly employed in the related art. Specifically, a compound having an unsaturated double bond and a compound having an epoxide group are dissolved in a nonaqueous or aqueous solvent, and reacted at −50 to 150° C. in the presence of a base such as amine. A reaction temperature below −50° C. may result in low reaction yield. And, a reaction temperature above 150° C. may result in the decomposition of the compounds. Hence, it is preferred that the aforesaid range be kept.

The compound having an unsaturated double bond may be one commonly used in the related art, and is not particularly limited. Specific examples include hydroxyethyl acrylate, hydroxyethyl methacrylate, methacryloyl chloride, 2,4-bisethyloxy methacrylate 6-chloro-1,3,5-triazine, 2-ethyloxy methacrylate 4,6-dichloro-1,3,5-triazine, 2,4-bisethylthioxy methacrylate 6-chloro-1,3,5-triazine, 2-ethylthioxy methacrylate 4,6-dichloro-1,3,5-triazine, diphenyl sulfide 4-ethyloxy methacrylate, 4'-carboxylic acid, monomethacrylate of polyalkylene glycol having $C_1$-$C_{20}$ alkylene, monoacrylate of polyalkylene glycol having $C_1$-$C_{20}$ alkylene, and the like. Also, the compound having an epoxide group may be one commonly used in the related art. Specific examples include a $C_1$-$C_{20}$ epoxy alkylene halide, wherein the halogen is bromine, chlorine, iodine, etc., e.g., epichlorohydrin (1-chloro-2,3-epoxypropane), 1-bromo-2,3-epoxypropane, 1-chloro-2-methyl-2,3-epoxypropane, 1-bromo-2,3-epoxypentane, 2-chloromethyl-2,2-epoxybutane, 1-bromo-4-methyl-3,4-epoxypentane, 1-bromo-4-ethyl-2,3-epoxypentane, 4-chloro-2-methyl-2,3-epoxypentane(4-chloro-2-methyl-2,3-epoxypentane), and so forth. Also, propylene glycol diglycidyl chloroalkyl bisphenol epoxide, chloroalkyl biphenyl epoxy resin, chloroalkyl bisphenol S epoxy resin, diglycidyl phthalate resin, and the like may be used.

The proportion of the compound having an unsaturated double bond and the compound having an epoxide group may be varied depending on the target compound. Specifically, a proportion with 0.1 to 5.0 mols of the compound having an epoxide group to 1 mol of the compound having an unsaturated double bond is preferred.

The base compound may be one commonly used in the related art, and is not particularly limited. Specific examples include triethylamine (TEA), tripropylamine (TPA), ethanolamine (EA), trioctylamine (TOA), pyridine, triethanolamine (TEA), NaOH, KOH, NaSH, 1,4-diazabicyclo[2.2.2]octane (DABCO), and so forth. The amine or base compound is used in an amount of from 0.1 to 10 parts by weight, based on 1 part by weight of the compound having an unsaturated double bond. When the amount is less than 0.1 part by weight or exceeds 10 parts by weight, the compound may not be obtained. Hence, it is preferred that the aforesaid range be kept.

A phase transfer catalyst may used as co-catalyst. Specifically, benzyltriethylammonium chloride (BTEAC), benzyltrimethylammonium chloride, cetyltrimethylammonium chloride, benzyltrimethylammonium tribromide, benzyltripropylammonium chloride or benzyltrimethylammonium bromide may be used. The phase transfer catalyst is used in an amount of from 0.01 to 5 parts by weight, based on 1 part by weight of the base compound. When the amount is less than 0.01 part by weight, the compound may not be obtained. And, when the amount exceeds 5 parts by weight, purification may become difficult. Hence, it is preferred that the aforesaid range be kept.

Such prepared photopolymerizable monomer of the formula (1) is polymerizable with light or heat, using a photo-curing agent or a thermal curing agent commonly used in the related art. The curing agent is used not more than 30 weight %, specifically from 1 to 30 weight %. If the amount is less than 1 weight %, curing will not be performed. Meanwhile, if the amount exceeds 30 weight %, a transparent photopolymer may not be obtained due to aggregation of the compounds. Hence, it is preferred that the aforesaid range be kept.

Particularly, the photopolymerizable monomer of the formula (1) according to the present invention provides superior photopolymerization efficiency and, thus, can be utilized effectively in coating, imaging and patterning.

The present invention is further characterized by a photo-curable composition comprising 1 to 99.99 weight % of the photopolymerizable monomer having the formula (1) and 0.01 to 99 weight % of an initiator.

The initiator may be one commonly used in the related art, and is not particularly limited. Specifically, a radical initiator such as Irgacure 184, Irgacure 784, Irgacure 819, Irgacure149, Irgacure 907, Irgacure 1700, Irgacure 1800, Irgacure 1850, Irgacure 2959, Irgacure 369, Irgacure 500 and Darocure; or a sulfonium salt, a phosphonium salt, an arsenate or an antimonite such as triphenylsulfonium hexafluorophosphorus, triphenylsulfonium hexafluoroarsenate, tiphenylsulfonium hexafluoroantimonate, diaryliodonium hexafluorophosphorus, diaryliodonium hexafluoroarsenate and diaryliodonium hexafluoroantimonate may be used.

If the initiator is used in an amount less than 0.01 weight %, photopolymerization may not occur. Meanwhile, if the amount exceeds 99 weight %, the degree of polymerization may decrease. Hence, it is preferred that the aforesaid range be kept.

The photocurable composition of the present invention may comprise various compounds generally used to improve physical properties. Specifically, an unsaturated monomer, a polymer resin, an organic solvent, a comonomer and a photosensitizer may be added.

The photocurable composition may further comprise an unsaturated monomer in order to improve the rate and efficiency of polymerization. The unsaturated monomer may be a vinylic or an acrylic monomer. Specific examples include

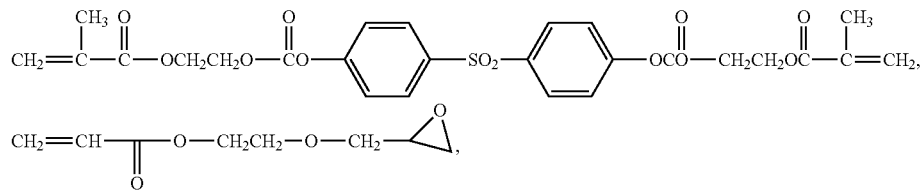

$CH_2=CH-C(=O)OCH_2CF_2CH_2OC(=O)-CH=CH_2$, $CH_2=CH-C(=O)O(CH_2CH_2O)_nC(=O)-CH=CH_2$ (wherein n is an integer 1 or larger), $CH_2=CH-C(=O)O(CH_2CH_2O)_nCH_2]_3C-CH_2CH_3$ (wherein n is an integer 1 or larger), $CH_2=CH-C(=O)SCH_2CH_2SCH_2CH_2S-C(=O)-CH=CH_2$,

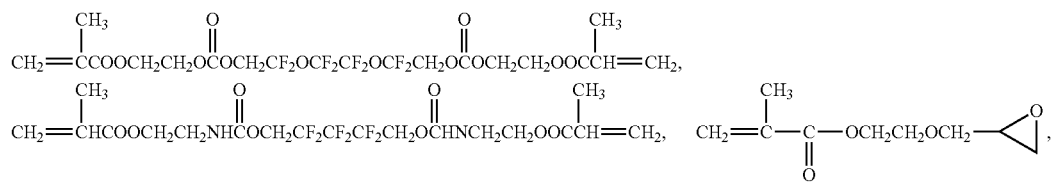

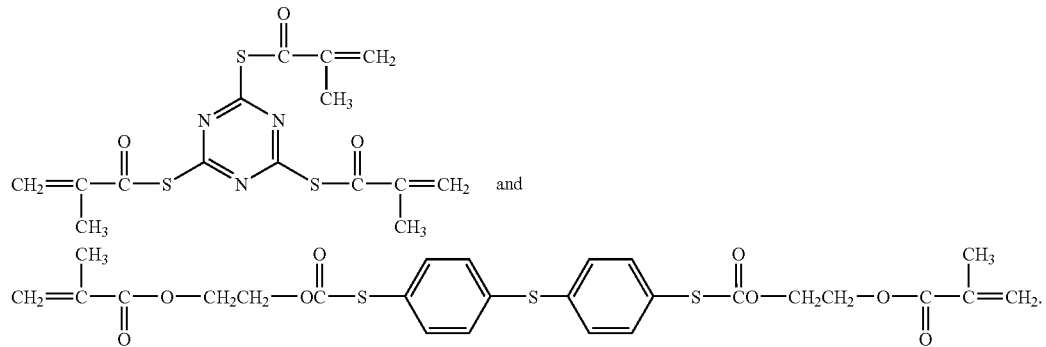

The unsaturated monomer is used in an amount of from 1 to 20 parts by weight, based on 1 part by weight of the photopolymerizable monomer of the formula (1). If the amount is less than 1 part by weight, the intended effect will not be obtained. Meanwhile, if the amount exceeds 20 parts by weight, physical properties may become poor. Hence, it is preferred that the aforesaid range be kept.

A polymer resin may be used to improve processability or physical properties of a film. Specifically, polyolefin, polycarbonate, polymethyl methacrylate, polyester, polyvinyl alcohol, polyimide, polysulfone, polybutyral, polyolefin, polyvinyl chloride resins) polyvinyl acetate resins, vinyl chloride-vinyl acetate copolymers, polystyrene resins, styrene copolymers, phenoxy resins, polyester resins, aromatic polyester resins, polyurethane resins, polycarbonate resins, polyacrylate resins, polymethacrylate resins, acrylic copolymers, maleic anhydride copolymers, polyvinyl alcohol resins, modified polyvinyl alcohol resins, hydroxyethyl cellulose resins, carboxymethyl cellulose resins, starches, or a mixture thereof may be used.

The polymer resin may be used in an amount of from 1 to 500 weight %, based on that of the photocurable composition. If the amount is less than 1 weight %, it becomes difficult to obtain the wanted property. Meanwhile, if the amount exceeds 500 weight %, the degree of photopolymerization may decrease. Hence, it is preferred that the aforesaid range be kept.

Chloroform or tetrachloroethane may be used as an organic solvent to control the concentration of the photocurable composition. Further, methanol, ethanol, isopropanol, n-butanol, methylisocarbinol, acetone, 2-butanone, ethyl amyl ketone, diacetone alcohols, isophorone, cyclohexanone, N,N-dimethylformamide, N,N-dimethylacetoamide, diethyl ether, diisopropyl ether, tetrahydrofuran, 1,4-dioxane, 3,4-dihydro-2H-pyran, 2-methoxyethanol, 2-ethoxyethanol, 2-butoxyethanol, ethylene glycol dimethyl ether, methyl acetate, ethyl acetate, isobutyl acetate, amyl acetate, ethyl lactate, ethylene carbonate, benzene, toluene, xylene, hexane, heptane, isooctane, cyclohexane, methylene chloride, 1,2-dichloroethane, dichloropropane, chlorobenzene, dimethyl sulfoxide, N-methyl-2-pyrrolidone, tetrachloroethane, N-octyl-2-pyrrolidone, etc., may be used.

The organic solvent is used in an amount of from 0.01 to 100 parts by weight, based on 1 part by weight of the monomer. If the amount is less than 0.01 part by weight, the intended effect may not be obtained. In contrast, if the amount exceeds 100 parts by weight, photopolymerization will not occur. Hence, it is preferred that the aforesaid range be kept.

A comonomer for enhancing the electrical and mechanical properties of the cured polymer may be used. Specifically, one or more of naphtyl-1-oxyethyl acrylate, 2-(N-carbazolyl-1-oxyethyl) acrylate, N-vinylcarbazole, isobornyl acrylate, phenoxyethyl acrylate, diethylene glycol monomethyl ether acrylate, diethylene glycol biscarbonate, allyl monomers, α-methylstyrene, styrene, divinylbenzene, polyethylene oxymethacrylate, polyethylene oxyacrylate, polyethylene oxydiacrylate, alkylene triacrylate and other previously known monomers having unsaturated groups may be used The comonomer is used in an amount of from 1 to 90 weight %, preferably from 5 to 50 weight %, based on the photocurable composition. When the amount is less than 1 weight %, adhesion to the substrate may be poor. Meanwhile, if the amount exceeds 90 weight %, the degree of polymerization may decrease. Hence, it is preferred that the aforesaid range be kept.

A photosensitizer may be used to accelerate photopolymerization. Specifically, at least one compound selected from anthracene, perylene, methyl red, methyl orange, methylene blue, pyran derivatives, acridine, mono-, di- or tri-halomethyl substituted triazine and quinazolinone may be used.

The photosensitizer is used in an amount of from 0.01 to 20 weight %, based on that of the photocurable composition. If the amount is less than 0.01 weight %, the photosensitizing effect may not be sufficient. In contrast, if the amount exceeds 20 weight %, a polymer with a low molecular weight will be produced. Hence, it is preferred that the aforesaid range be kept.

In addition, expanding monomers, layered silicate, nanopowder, liquid crystals, dyes, etc., may be used. And, in order to improve thermal, mechanical and processing properties, various additives and fillers, including commonly used antioxidant, dye, pigment, lubricant, thickener, etc., may be added. The composition of the present invention may further comprise a polymerization catalyst for promoting polymerization and/or a UV absorbent, an anticolorant, etc., for improving weather resistance.

Such components may be used in an adequate amount within the range not departing from the scope of the present invention.

The photocurable composition may be coated, for example, on a substrate such as silicon wafer, glass plate, plastic film, quarts, etc., and dried in a temperature range from −20 to 100° C., preferably from room temperature to 80° C. to form a film. If necessary, the composition may be filled in a mold, and dried preferably at a temperature below about 80° C. to obtain a molded product.

The coating may be performed by any method commonly used in the related art. Solution coating methods, for example, spin coating, flow coating, bar coating, screen coating, spray coating, etc., are preferred.

The coated photopolymer maintains a film structure. Such a photopolymerizable film may be grated by two-beam coupling. The degree of photopolymerization can be identified by the grating. The film thickness may be varied depending on the particular purpose. Although not intending to be particularly limited, the thickness may range from 0.0001 to 30 mm.

As described above, the photopolymerizable monomer of the present invention can be prepared into photopolymer film without using a particular solvent, and needs no additional process such as drying or cleaning after the film formation. Also, an in-line process is possible because of very short reaction time, thereby simplifying the film formation process. Besides, because it has superior mechanical properties and adhesion, and can be prepared into solid films, it is applicable to any solid-type devices. Further, the polymer film of the present invention may be prepared by light radiation followed by heat treatment, or by coating on lithium foil, aluminum foil or lithium-copper foil.

Accordingly, the photopolymerizable monomer and the photocurable composition according to the present invention, which are polymerizable by light or heat, can be utilized in pattern formation, organic semiconductors, display devices, multi-grating, printing films, photoresist films, information recording films, optical filter lenses, anti-forgery films and coatings, encapsulating agents, plastic containers, medicines, and the like.

EXAMPLES

The following examples illustrate the present invention in more detail but they should not be construed as limiting the scope of the present invention.

Example 1

Compound 1-1

To 5 g (0.0384 mol) of hydroxyethyl methacrylate (HEMA) dissolved in methylene chloride, 3.88 g (0.0384 mol) of triethylamine (TEA) was added, and the mixture was stirred for 10 minutes. Then, the mixture was added with 4.92 g (0.0384 mol) of 4-chlorophenol and stirred again. 24 hours later, after washing several times with distilled water, the organic layer was separated and the solvent was removed by washing several times with 1 wt % aqueous hydrochloric acid solution. The remainder was purified by chromatography using hexane and ethyl acetate (1:1, w/w). Then, after adding an aqueous solution of 1.26 g (0.0225 mol) of KOH and adding 0.1 g of a phase transfer catalyst BTEAC, 4.14 g (0.0225 mol) of epichlorohydrin was added, and stirred at room temperature. 24 hours later, after extracting with chloroform, the solution was washed several times with distilled water. Subsequently, epichlorohydrin and the solvent were evaporated at 70° C. The remainder was purified by chromatography using hexane and ethyl acetate (1:1, w/w). Compound 1-1 was obtained with a 99% or better of purity (yield=64%).

$^1$H NMR (300 MHz, CDCl$_3$): d 1.93 ppm (s, 3H), 2.38/2.63/3.04 ppm (m, 3H, epoxide), 3.95-4.57 (m, 6H, —CH$_2$—CH$_2$—), 5.58/6.15 ppm (m, 3H, —HC═CH$_2$), 6.66 ppm (m, Ar, 4H)

IR: 840, 1637, 1725, 3000

Mass: 278.12

Polymerization efficiency: A photopolymer film was prepared using thus obtained Compound 1-1 (2 g), Irgacure 784 (0.02 g) and polysulfone (4 g) and radiating 491-nm laser. Photopolymerization efficiency was 80% or higher.

Example 2

Compound 1-2

To 5 g of hydroxyethyl methacrylate (HEMA) dissolved in methylene chloride, 4.2 g of tripropylamine (TPA) was added, and stirred for 10 minutes. Then, the mixture was stirred further after adding with 5.53 g of 4-chlorobenzene-1,2-diol. 24 hours later, after washing several times with distilled water, the organic layer was separated and the solvent was removed by washing several times with 1 wt % aqueous hydrochloric acid solution. The remainder was purified by chromatography using hexane and ethyl acetate (2:1, w/w). Then, after adding an aqueous solution of 2.35 g of KOH and adding 0.1 g of a phase transfer catalyst BTEAC, 3.864 g of epichlorohydrin was added, and stirred at room temperature. 24 hours later, after extracting with chloroform, the solution was washed several times with distilled water. Subsequently, epichlorohydrin and the solvent were evaporated at 70° C. The remainder was purified by chromatography using hexane and ethyl acetate (2:1, w/w). Compound 1-2 was obtained with 99% or better of purity (yield=45%).

$^1$H NMR (300 MHz, CDCl$_3$): d 1.93 ppm (s, 3H), 2.38/2.63/3.04 ppm (m, 6H, epoxide), 3.95-4.57 (m, 8H, —CH$_2$—CH$_2$—), 5.58/6.15 ppm (m, 3H, —HC=CH2), 6.17-6.55 ppm (m, Ar, 3H)

IR: 840, 1637, 1725, 3000

Mass: 350.14

Polymerization efficiency: A 20-μm thick, transparent film was prepared using thus obtained Compound 1-2 (1 g), the unsaturated comonomer (3 g) described below, the photoacid generator (0.02 g) described below and Irgacure 184 (Aldrich, 0.05 g), applying the mixture on a slide glass, and radiating 20-mW UV at room temperature for 5 minutes. Photopolymerization efficiency was 90% or higher.

Unsaturated comonomer:

$$CH_2=\overset{CH_3}{\underset{}{C}}-\underset{O}{\overset{}{C}}-OCH_2CH_2OCH_2-\triangleleft^O$$

Photoacid generator:

[structure: diphenyliodonium with —O—C$_8$H$_{17}$ group, $^-$OTs]

where Ts is trifluoromethanesulfonate.

Example 3

Compound 1-3

To 5 g of hydroxyethyl methacrylate (HEMA) dissolved in methylene chloride, 3 g of pyridine was added, and stirred for 10 minutes. Then, the mixture was stirred further after adding with 5.53 g of 4-chlorobenzene-1,3-diol. 24 hours later, after washing several times with distilled water, the organic layer was separated and the solvent was removed by washing several times with 1 wt % aqueous hydrochloric acid solution. The remainder was purified by chromatography using hexane and ethyl acetate (3:1, w/w). Then, after adding an aqueous solution of 2.35 g (0.042 mol) of KOH and adding 0.1 g of cetyltrimethylammonium chloride and 0.1 g of benzyltrimethylammonium tribromide, 3.864 g (0.042 mol) of epichlorohydrin was added, and stirred at room temperature. 24 hours later, after extracting with chloroform, the solution was washed several times with distilled water. Subsequently, after evaporation of the liquid at 70° C. followed by purification, Compound 1-3 was obtained with a 99% or better of purity (yield=60%).

$^1$H NMR (300 MHz, CDCl$_3$): d 1.93 ppm (s, 3H), 2.38/2.63/3.04 ppm (m, 6H, epoxide), 3.95-4.20 (m, 4H, —CH$_2$—CH$_2$—), 5.58/6.15 ppm (m, 3H, —HC=CH$_2$), 6.17-6.55 ppm (m, Ar, 3H)

IR: 840, 1637, 1725, 3000

Mass: 350.14

Polymerization efficiency: A 9-μm thick, transparent film was prepared using thus obtained Compound 1-3 (1 g), the unsaturated monomer (3 g) described below, the photoacid generator (0.02 g) described below and Irgacure 784 (Aldrich, 0.05 g), applying the mixture on a slide glass, and radiating 10-mW, 491-nm laser at room temperature for 10 minutes. Photopolymerization efficiency was 90% or higher.

Unsaturated monomer:

$$CH_2=CH-\underset{O}{\overset{}{C}}-O-CH_2CH_2-O-CH_2-\triangleleft^O$$

Photoacid generator:

[structure: diphenyliodonium with —O—C$_{12}$H$_{25}$ group, $^-$OTs]

wherein Ts is trifluoromethanesulfonate.

Example 4

Compound 1-4

To 10 g (0.0768 mol) of hydroxyethyl methacrylate (HEMA) dissolved in methylene chloride, 7.76 g (0.0768 mol) of triethylamine (TEA) was added, and stirred for 10 minutes. Then, the mixture was stirred further after adding with 6.22 g (0.0384 mol) of 2,4-dichlorophenol. 24 hours later, after washing several times with distilled water, the organic layer was separated and the solvent was removed by washing several times with 1 wt % aqueous hydrochloric acid solution. The remainder was purified by chromatography using hexane and ethyl acetate (3:1.2, w/w). Then, after adding an aqueous solution of 0.8 g (0.0143 mol) of KOH and adding 0.1 g of a phase transfer catalyst BTEAC, 1.32 g (0.0143 mol) of epichlorohydrin was added, and stirred at room temperature. 24 hours later, after extracting with chloroform, the solution was washed several times with distilled water. Subsequently, after evaporation of the liquid at 70° C. followed by purification, Compound 1-4 was obtained with a 99% or better of purity (yield=50%).

$^1$H NMR (300 MHz, CDCl$_3$): d 1.93 ppm (s, 6H), 2.38/2.63/3.04 ppm (m, 6H, epoxide), 4.22-4.57 (m, 8H, —CH$_2$—CH$_2$—), 5.58/6.15 ppm (m, 6H, —HC=CH$_2$), 6.17-6.55 ppm (m, Ar, 3H)

IR: 840, 1637, 1725, 3000

Mass: 406.1

Polymerization efficiency: A photopolymer film was prepared using a composition comprising thus obtained Compound 1-4 (0.1 g), the unsaturated monomer (2 g) described below, the photoacid generator (0.01 g) described below, Irgacure 784 (Aldrich, 0.02 g), polysulfone (8 g) and chloroform (40 mL), applying the composition on a slide glass, and then removing the solvent. Through two-beam coupling using 491-nm laser, a grating pattern as shown in FIG. 1 was obtained. Grating spacing was 0.9 μm, photopolymerization efficiency was 75%, and shrinkage was 0.2%.

Unsaturated monomer:

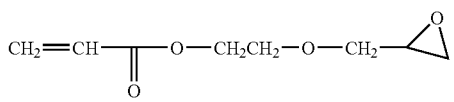

Photoacid generator:

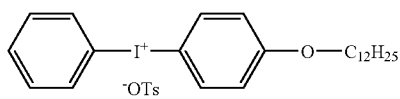

where Ts is trifluoromethanesulfonate.

Example 5

Compound 1-5

To 5 g (0.02 mol) of 4-(4-hydroxyphenylsulfonyl)phenol dissolved in chloroform, 2.022 g (0.02 mol) of triethylamine (TEA) was added, and stirred for 10 minutes. Then, the mixture was stirred further after adding with 2.08 g (0.02 mol) of methacryloyl chloride. 24 hours later, after washing several times with distilled water, the organic layer was separated and the solvent was removed by washing several times with 1 wt % aqueous hydrochloric acid solution. The remainder was purified by chromatography using hexane and ethyl acetate (5:2, w/w). Then, after adding an aqueous solution of 0.88 g (0.0157 mol) of KOH and adding 0.1 g of a phase transfer catalyst BTEAC, 1.44 g (0.0157 mol) of epichlorohydrin was added, and stirred at room temperature. 24 hours later, after extracting with chloroform, the solution was washed several times with distilled water. Subsequently, after evaporation of the liquid at 70° C. followed by purification, Compound 1-5 was obtained with a 99% or better of purity (yield=70%).

$^1$H NMR (300 MHz, CDCl$_3$): d1.93 ppm (s, 3H), 2.38/2.63/3.04 ppm (m, 3H, epoxide), 3.95-4.20 (m, 2H, —CH$_2$—CH$_2$—), 5.49/5.98 ppm (m, 3H, —HC=CH$_2$), 6.94-7.79 ppm (m, Ar, 8H)

IR: 840, 1340, 1637, 1725, 3000

Mass: 374.08

Polymerization efficiency (thermal polymerization): A 30-μm thick, transparent film was prepared using a composition comprising thus obtained Compound 1-5 (0.06 g), Compound 1-1 (0.1 g), the unsaturated monomer (0.8 g) described below and azobisisobutyronitrile (AIBN, 0.1 g), applying the composition on a stainless steel plate, and performing reaction at 120° C. for 24 hours. Photopolymerization efficiency was 70%, and Rockwell hardness of the obtained film was 110 (L scale).

Unsaturated monomer:

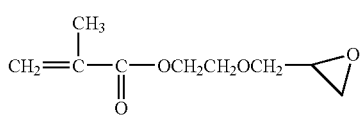

Example 6

Compound 1-6

To 2.275 g (0.0175 mol) of hydroxyethyl methacrylate (HEMA) dissolved in methylene chloride, 1.77 g (0.0175 mol) of triethylamine (TEA) was added, and stirred for 10 minutes. Then, the mixture was stirred further after adding with 5 g (0.0175 mol) of 1-(4-chlorophenylsulfonyl)-4-chlorobenzene. 24 hours later, after washing several times with distilled water, the organic layer was separated and the solvent was removed by washing several times with 1 wt % aqueous hydrochloric acid solution. The remainder was purified by chromatography using toluene and ethyl acetate (2:1, w/w). Then, after adding an aqueous solution of 0.88 g (0.0157 mol) of KOH and adding 0.1 g of a phase transfer catalyst BTEAC, 1.21 g (0.01315 mol) of epichlorohydrin was added, and stirred at room temperature. 24 hours later, after extracting with chloroform, the solution was washed several times with distilled water. Subsequently, after evaporation of the liquid at 80° C. followed by purification, Compound 1-6 was obtained with a 99% or better of purity (yield=75%).

$^1$H NMR (300 MHz, CDCl$_3$): d 1.93 ppm (s, 3H), 2.38/2.63/3.04 ppm (m, 3H, epoxide), 3.95-4.57 (m, 6H, —CH$_2$—CH$_2$—), 5.58/6.15 ppm (m, 3H, —HC=CH$_2$), 6.94-7.79 ppm (m, Ar, 8H)

IR: 840, 1340, 1637, 1725, 3000

Mass: 642.73

Polymerization efficiency: A photopolymer film was prepared using a composition comprising thus obtained Compound 1-6 (0.1 g), the unsaturated monomer (2 g) described below, the photoacid generator (0.01 g) described below, Irgacure 784 (Aldrich, 0.02 g), methyl red (0.005 g), polysulfone (8 g) and chloroform (40 mL), applying the composition on a slide glass, removing the solvent, and performing polymerization for 10 minutes using 30-mW, 514-nm laser. Photopolymerization efficiency was 90% or higher.

Unsaturated monomer:

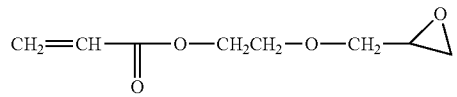

Photoacid generator:

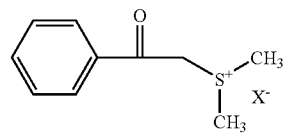

wherein X=SbF$_6$.

Example 7

Compound 1-7

To 5 g (0.02 mol) of 4-(4-hydroxyphenylsulfonyl)phenol dissolved in DMF, an aqueous solution of 2.24 g (0.04 mol) of NaSH was added, and stirred for 24 hours. Dithiol was obtained after washing several times with 1 wt % aqueous hydrochloric acid solution and filtering. Thus obtained dithiol was dissolved in methylene chloride, and after adding 1.79 g (0.0177 mol) of triethylamine (TEA) and stirring for 10 minutes, 1.84 g (0.0177 mol) of methacryloyl chloride was added and stirred. 40 hours later, after washing several times with distilled water, the organic layer was separated and the solvent was removed by washing several times with 1 wt % aqueous hydrochloric acid solution. The remainder was purified by chromatography using hexane and ethyl acetate (1:2, w/w). Then, after adding an aqueous solution of 0.6 g of NaOH and adding 0.1 g of benzyltripropylammonium chloride, 1.26 g (0.0137 mol) of epichlorohydrin was added, and stirred at room temperature. 48 hours later, after extracting with chloroform, the solution was washed several times with distilled water. Subsequently, after evaporation of the liquid at 70° C. followed by purification, Compound 1-7 was obtained with a 99% or better of purity.

Mass: 420.05

Photopolymerization efficiency (UV photopolymerization): 80%.

Example 8

Compound 1-8

To 2.925 g (0.0225 mol) of hydroxyethyl methacrylate (HEMA) dissolved in methylene chloride, 2.27 g (0.0225 mol) of triethylamine (TEA) was added, and stirred for 10 minutes. Then, the mixture was stirred further after adding with 5 g (0.0225 mol) of dibenzyl chloride. 24 hours later, after washing several times with distilled water, the organic layer was separated and the solvent was removed by washing several times with 2 wt % aqueous hydrochloric acid solution. The remainder was purified by chromatography using hexane and ethyl acetate (1:1, w/w). Then, after adding an aqueous solution of 0.9 g (0.0158 mol) of KOH and adding 0.1 g of a phase transfer catalyst BTEAC, 1.453 g (0.0158 mol) of epichlorohydrin was added, and stirred at room temperature. 39 hours later, after extracting with dichloromethane, the solution was washed several times with distilled water. Subsequently, after evaporation of the liquid in a rotary evaporator followed by purification, Compound 1-8 was obtained with a 99% or better of purity (yield=75%).

$^1$H NMR (300 MHz, CDCl$_3$): d 1.93 ppm (s, 3H), 2.38/2.63/3.04 ppm (m, 3H, epoxide), 2.86-4.57 (m, 6H, —CH$_2$—CH$_2$—), 5.58/6.15 ppm (m, 3H, —HC=CH$_2$), 6.83-7.37 ppm (m, Ar, 8H)

IR: 840, 1637, 1725, 3000

Mass: 354.15

Polymerization efficiency: A 20-μm thick photopolymer film was prepared using a composition comprising thus obtained Compound 1-8 (0.1 g), the unsaturated monomer (2 g) described below, the photoacid generator (0.01 g) described below, Irgacure 784 (Aldrich, 0.02 g), polymethyl methacrylate (PMMA, 7 g), chloroform (40 mL) and tetrachloroethane (5 mL), applying the composition on a slide glass, and removing the solvent. A grating pattern was obtained through two-beam coupling using 491-nm laser. Grating spacing was 0.9 μm, and photopolymerization efficiency was 70%.

Unsaturated monomer:

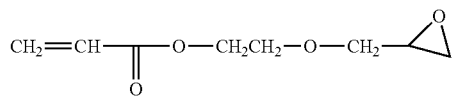

Photoacid generator:

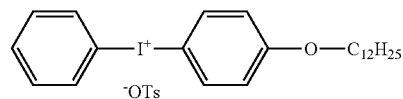

wherein Ts is trifluoromethanesulfonate.

Example 9

Compound 1-9

To 5 g (0.0225 mol) of dibenzyl chloride dissolved in DMF, an aqueous solution of 1.26 g (0.0225 mol) of NaSH was added, and stirred for 24 hours. Dithiol was obtained after washing several times with 1 wt % aqueous hydrochloric acid solution and filtering. Thus obtained dithiol was dissolved in methylene chloride, and after adding 1.5 g (0.0148 mol) of triethylamine (TEA) and stirring for 10 minutes, 1.54 g (0.0148 mol) of methacryloyl chloride was added and stirred. 24 hours later, after washing several times with distilled water, the organic layer was separated and the solvent was removed by washing several times with 1 wt % aqueous hydrochloric acid is solution. The remainder was purified by chromatography using hexane and ethyl acetate. Then, after adding an aqueous solution of 0.9 g (0.0158 mol) of KOH and adding 0.1 g of a phase transfer catalyst BTEAC, 1.453 g (0.0158 mol) of epichlorohydrin was added, and stirred at room temperature. 36 hours later, after extracting with chloroform, the solution was washed several times with distilled water. Subsequently, after evaporation of epichlorohydrin and the solvent followed by chromatography using hexane and ethyl acetate (2:1, w/w), Compound 1-9 was obtained with a 99% or better of purity (yield=75%).

$^1$H NMR (300 MHz, CDCl$_3$): d 1.93 ppm (s, 3H), 2.38/2.63/2.81 ppm (m, 3H, epoxide), 2.78-3.03 (m, 2H, —CH$_2$—CH$_2$—), 5.77/5.88 ppm (m, 3H, —HC=CH$_2$), 7.24-7.32 ppm (m, Ar, 8H)

IR: 840, 1340, 1637, 1725, 3000

Mass: 342.07

Polymerization efficiency (photopolymerization): 70% or higher.

Example 10

Compound 1-10

To 5 g (0.027 mol) of dibenzyl alcohol dissolved in methylene chloride, 2.73 g (0.027 mol) of triethylamine (TEA) was added, and stirred for 10 minutes. Then, the mixture was stirred further after adding with 2.81 g (0.027 mol) of methacryloyl chloride. 24 hours later, after washing several times with distilled water, the organic layer was separated and the solvent was removed by washing several times with 1 wt % aqueous hydrochloric acid solution. The remainder was purified by chromatography using chloroform. Then, after adding an aqueous solution of 0.9 g (0.0158 mol) of KOH and adding 0.1 g of a phase transfer catalyst BTEAC, 1.453 g (0.0158 mol) of epichlorohydrin was added, and stirred at room temperature. 24 hours later, after extracting with chloroform, the solution was washed several times with distilled water. Subsequently, after evaporation of epichlorohydrin and the solvent at 70° C. followed by chromatography using hexane and ethyl acetate (2:1, w/w), Compound 1-10 was obtained with a 99% or better of purity (yield=75%).

$^1$H NMR (300 MHz, CDCl$_3$): d 1.93 ppm (s, 3H), 2.38/2.63/3.04 ppm (m, 3H, epoxide), 3.95-4.20 (m, 2H, —CH$_2$—CH$_2$—), 5.71/6.26 ppm (m, 3H, —HC=CH$_2$), 6.83-7.37 ppm (m, Ar, 8H)

IR: 840, 1340, 1637, 1725, 3000
Mass: 310.12
Photopolymerization efficiency (thermal polymerization): 82% or higher (90° C., 24 hours, initiator=benzoyl peroxide, solvent=acetonitrile).

Example 11

Compound 1-11

To 5 g (0.0148 mol) of sulfonyl ether dialcohol dissolved in methylene chloride, 1.5 g (0.0148 mol) of triethylamine (TEA) was added, and stirred for 10 minutes. Then, the mixture was stirred further after adding with 1.54 g (0.0148 mol) of methacryloyl chloride. 24 hours later, after washing several times with distilled water, the organic layer was separated and the solvent was removed by washing several times with 1 wt % aqueous hydrochloric acid solution. The remainder was purified by chromatography using hexane and ethyl acetate (3:2, w/w). Then, after adding an aqueous solution of 0.66 g (0.0119 mol) of KOH and adding 0.1 g of a phase transfer catalyst BTEAC, 1.1 g (0.0119 mol) of epichlorohydrin was added, and stirred at room temperature. 24 hours later, after extracting with chloroform, the solution was washed several times with distilled water. Subsequently, after evaporation of epichlorohydrin and the solvent at 70° C. followed by chromatography using hexane and ethyl acetate (1:1, w/w), Compound 1-11 was obtained with a 99% or better of purity (yield=70%).

$^1$H NMR (300 MHz, CDCl$_3$): d 1.93 ppm (s, 3H), 2.38/2.63/3.04 ppm (m, 3H, epoxide), 2.86-4.57 (m,10H, —CH$_2$—CH$_2$—), 5.58/6.15 ppm (m, 3H, —HC=CH$_2$), 6.94-7.79 ppm (m, Ar, 8H)

IR: 840, 1340, 1637, 1725, 3000
Mass: 462.13
Polymerization efficiency: 87% or higher.

Example 12

Compound 1-12

To 5 g (0.0273 mol) of 2,4,6-trichloro-1,3,5-triazine dissolved in acetone, a solution of 4.62 g (0.0273 mol) of diphenylamine dissolved in a mixture of 23 g of acetone and 1 g of water was added, and reaction was performed at 0° C. 2 hours later, after filtration and recrystallization in ethanol, a highly pure intermediate was obtained. The intermediate was added to a solution of 2.275 g (0.0175 mol) of hydroxyethyl methacrylate (HEMA) dissolved in methylene chloride and to which 1.77 g (0.0175 mol) of triethylamine (TEA) had been added, and stirred. 24 hours later, after washing several times with distilled water, the organic layer was separated and the solvent was removed by washing several times with 1 wt % aqueous hydrochloric acid solution. The remainder was purified by chromatography using diethyl ether. Then, after adding an aqueous solution of 0.88 g (0.0157 mol) of KOH and adding 0.1 g of a phase transfer catalyst BTEAC, 1.4 g (0.0157 mol) of epichlorohydrin was added, and stirred at room temperature. 24 hours later, after extracting with chloroform, the solution was washed several times with distilled water. Subsequently, after evaporation of epichlorohydrin and the solvent at 70° C. followed by chromatography using hexane and ethyl acetate (1:1, w/w), Compound 1-12 was obtained with a 99% or better of purity (yield=75%).

$^1$H NMR (300 MHz, CDCl$_3$): d 1.73 ppm (s, 3H), 2.38/2.63/2.81 ppm (m, 3H, epoxide), 2.95/3.18 ppm (m ,2H), 4.77/4.88 ppm (m, 3H, —HC=CH$_2$), 6.46-7.01 ppm (m, Ar, 10H)

IR: 840, 1340, 1637, 1725, 2150, 3000
Mass: 448.17
Polymerization efficiency (thermal polymerization): 80% or higher.

Example 13

Compound 1-13

To 5 g (0.0273 mol) of 2,4,6-trichloro-1,3,5-triazine dissolved in acetone, a solution of 4.62 g (0.0273 mol) of diphenylamine dissolved in a mixture of acetone and water was added, and reaction was performed at 0° C. 2 hours later, after filtration and recrystallization in ethanol, a highly pure intermediate was obtained. The intermediate was dissolved in DMF, and after adding an aqueous of 1.26 g (0.0225 mol) of NaSH, stirred for 24 hours. Dithiol was obtained after washing several times with 1 wt % aqueous hydrochloric acid solution and filtering. Thus obtained dithiol was dissolved in methylene chloride, and after adding 1.5 g (0.0148 mol) of triethylamine (TEA) and stirring for 10 minutes, 1.54 g (0.0148 mol) of methacryloyl chloride was added and stirred. 24 hours later, after washing several times with distilled water, the organic layer was separated and the solvent was removed by washing several times with 1 wt % aqueous hydrochloric acid solution. The remainder was purified by chromatography using hexane and ethyl acetate. Then, after adding an aqueous solution of 0.9 g (0.0158 mol) of KOH and adding 0.1 g of a phase transfer catalyst BTEAC, 1.53 g of 1-chloro-2-methyl-2,3-epoxypropane was added, and stirred at room temperature. 18 hours later, after extracting with chloroform, the solution was washed several times with distilled water. Subsequently, after evaporation of epichlorohydrin and the solvent at 70° C. followed by chromatography using hexane and ethyl acetate (2:1, w/w), Compound 1-13 was obtained with a 99% or better of purity (yield=75%).

$^1$H NMR (300 MHz, CDCl3): d 1.73 ppm (s, 3H), 2.38/2.63/2.81 ppm (m, 3H, epoxide), 2.93/3.18 ppm (m ,2H), 4.77/4.88 ppm (m, 3H, —HC=CH$_2$), 6.46-7.01 ppm (m, Ar, 10H)

IR: 840, 1340, 1637, 1725, 2150, 3000
Polymerization efficiency (UV polymerization): 70% or higher.

Example 14

Compound 1-14

To 10 g (0.0768 mol) of hydroxyethyl methacrylate (HEMA) dissolved in methylene chloride, 7.76 g (0.0768 mol) of triethylamine (TEA) was added, and stirred for 10 minutes. Then, the mixture was stirred further after adding with 6.22 g (0.0384 mol) of 2,4-dichlorophenol. 24 hours later, after washing several times with distilled water, the organic layer was separated and the solvent was removed by washing several times with 2 wt % aqueous hydrochloric acid solution. The remainder was purified by chromatography using hexane and ethyl acetate (5:1, w/w). Then, after adding an aqueous solution of 0.8 g (0.0143 mol) of KOH and adding 0.1 g of a phase transfer catalyst BTEAC, 1.32 g (0.0143 mol) of 1-bromo-2,3-epoxypropane was added, and stirred at room temperature. 24 hours later, after extracting with chloroform, the solution was washed several times with distilled water. Subsequently, after evaporation of epichlorohydrin and the solvent at 70° C. followed by chromatography using hexane and ethyl acetate (2:1, w/w), Compound 1-14 was obtained with a 99% or better of purity (yield=55%).

$^1$H NMR (300 MHz, CDCl$_3$): d 1.93 ppm (s, 6H), 2.38/2.63/3.04 ppm (m, 6H, epoxide), 4.22-4.57 (m, 8H, —CH$_2$—CH$_2$—), 5.58/6.15 ppm (m, 6H, —HC=CH$_2$), 6.17-6.55 ppm (m, Ar, 3H)

IR: 840, 1637, 1725, 3000
Mass: 406.1
Polymerization efficiency (laser polymerization): 70% (491-nm laser photopolymerization).

Example 15

Compound 1-15

To 10 g of 2-hydroxyethyl acrylate dissolved in 100 mL of chloroform, 5 g of 1,4-diazabicyclo[2.2.2]octane (DABCO) was added, and stirred at 40° C. for 1 hour. Then, stirring was performed at 50° C. after adding 10 g of diphenyl sulfide 4,4'-dicarboxylic acid. 10 hours later, after washing several times with distilled water, the organic layer was separated and the solvent was removed by washing several times with 5 wt % aqueous acetic acid solution. After adding an aqueous solution of 0.8 g (0.0143 mol) of KOH and adding 0.1 g of BTEAC, 10 g of 3-glycidoxypropanol was added, and stirred at 50° C. 10 hours later, after extracting with chloroform, the solution was washed several times with distilled water. Subsequently, after evaporation of epichlorohydrin and the solvent at 70° C. followed by chromatography using hexane and ethyl acetate (2:1, w/w), Compound 1-15 was obtained with a 99% or better of purity (yield=45%).

$^1$H NMR (300 MHz, CDCl$_3$): d 1.93 ppm (s, 6H), 2.38/2.63/3.04 ppm (m, 6H, epoxide), 4.22-4.57 (m, 8H, —CH$_2$—CH$_2$—), 5.58/6.15 ppm (m, 6H, —HC=CH$_2$), 6.17-6.55 ppm (m, Ar, 3H)

IR: 840, 1637, 1725, 3000

Mass: 406.1

Polymerization efficiency (laser polymerization): 60% (491-nm laser photopolymerization).

The photopolymers prepared in Examples 1 to 15 were subject to the measurement of polymerization efficiency, adhesion strength, mechanical property (shrinkage) and transparency. The result is given in Table 1 below. Polymerization efficiency, mechanical property and transparency were measured as follows.

Mechanical property (1) Polymerization efficiency (%): Polymerization efficiency (conversion efficiency) was determined from the change of C=C vibration frequency band bound to unsaturated groups at 1550 to 1650 cm$^{-1}$ in IR spectroscopy.

Polymerization efficiency (%)=(C=C peak intensity after polymerization)/(C=C peak intensity before polymerization)×100    Equation 1

(2) Adhesion strength: Rockwell hardness was measured according to ASTM758.

Rockwell hardness (a)=150−RB wherein RB is the total indentation under load.

(3) Shrinkage (%): 100×(Thickness before curing−Thickness after curing)/(Thickness before curing)

(4) Transparency (%): Transmittance was measured at 600 nm using a UV-VIS spectrometer.

The invention has been described in detail with reference to preferred embodiments thereof. However, it will be appreciated by those skilled in the art that changes may be made in these embodiments without departing from the principles and scope of the invention the scope of which is defined in the appended claims and their equivalents.

What is claimed is:

1. A photopolymerizable monomer of the following formula(1):

$$\left[ \text{CH}_2=\overset{R^1}{\underset{\underset{O}{\|}}{C}}-\!\!\!-\!\!\!-(\text{CH}_2)_{\overline{Q}}X\!-\!\!(R^2-Y)_{\overline{L}}\right]_{\!\!M}\!\!R^3\!\!\left[\!Z-R^4-\!\!\triangleleft^{O}\right]_{\!\!N} \quad (1)$$

wherein
R$^1$ is H or CH$_3$;
R$^2$ is C$_1$-C$_{20}$ alkylene;
R$^3$ is phenylene, biphenylene, diphenylsulfone, or diphenylamino-triazinyl ;

R$^4$ is C$_1$-C$_{20}$ alkylene or C$_2$-C$_{20}$ alkyleneoxyalkyl;
X is O or S;
Y and Z are independently O, S, O—C=O or S—C=O;
L is 0 or an integer of 1 to 3;
M and N are independently an integer of 1 to 3; and
q is 0 or an integer of 1 to 30.

TABLE 1

| Example | Compound | Polymerization efficiency (%) | Adhesion strength (Rockwell hardness, M) | Shrinkage (%) | Transparency (%) |
|---|---|---|---|---|---|
| 1 | Compound 1-1 | 80 | 110 | 0.8 | 90 |
| 2 | Compound 1-2 | 90 | 114 | 0.67 | 87 |
| 3 | Compound 1-3 | 90 | 114 | 0.67 | 87 |
| 4 | Compound 1-4 | 75 | 121 | 0.67 | 87 |
| 5 | Compound 1-5 | 70 | 93 | 1.1 | 93 |
| 6 | Compound 1-6 | 90 | 90 | 0.68 | 110 |
| 7 | Compound 1-7 | 80 | 100 | 0.5 | 94 |
| 8 | Compound 1-8 | 70 | 108 | 0.9 | 92 |
| 9 | Compound 1-9 | 70 | 75 | 0.5 | 90 |
| 10 | Compound 1-10 | 80 | 103 | 0.9 | 92 |
| 11 | Compound 1-11 | 108 | 92 | 0.9 | 90 |
| 12 | Compound 1-12 | 80 | 87 | 0.2 | 88 |
| 13 | Compound 1-13 | 70 | 85 | 0.5 | 80 |
| 14 | Compound 1-14 | 70 | 117 | 0.35 | 93 |
| 15 | Compound 1-15 | 60 | 119 | 0.5 | 90 |

2. The photopolymerizable monomer according to claim 1, which is selected from
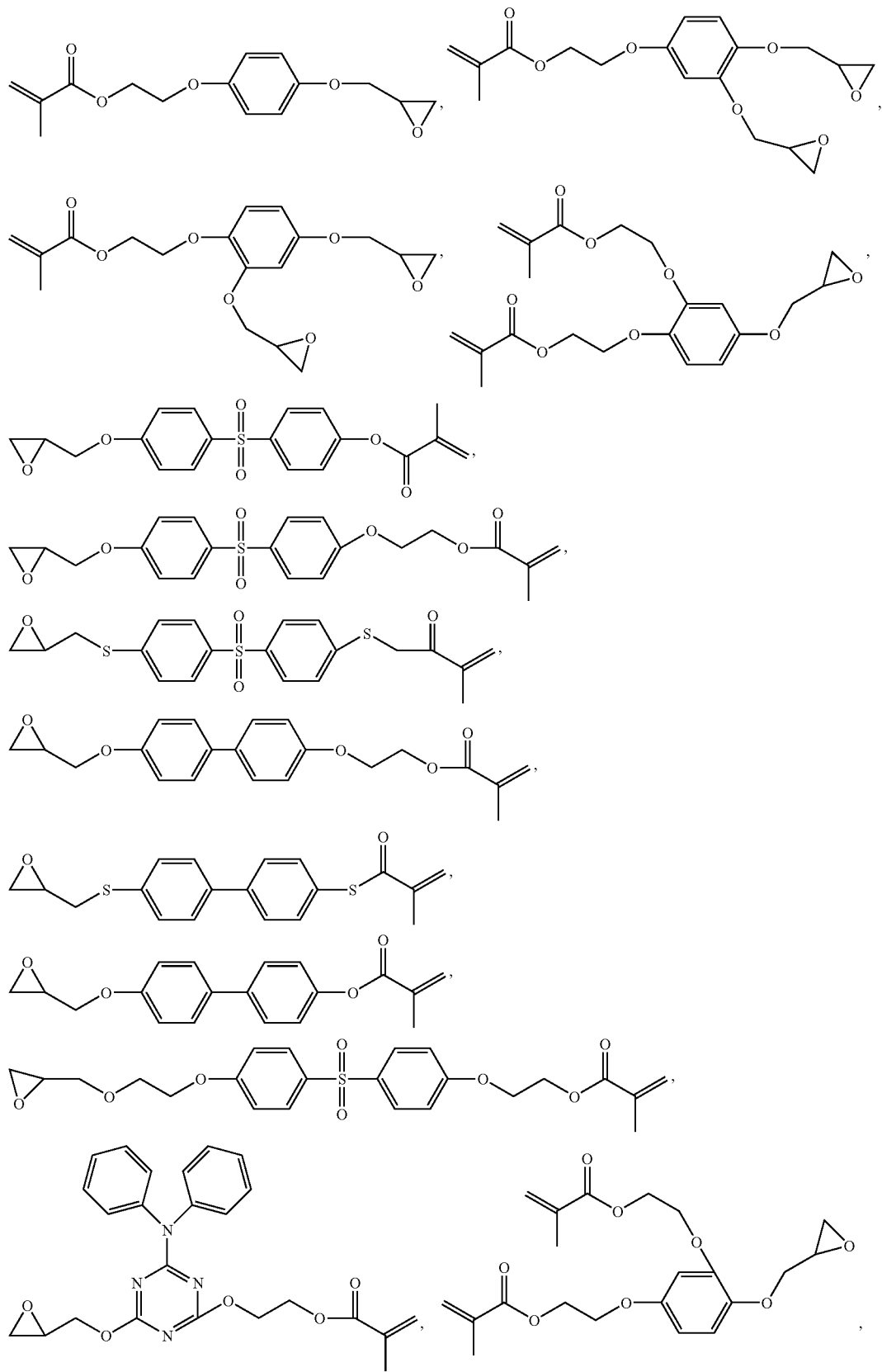

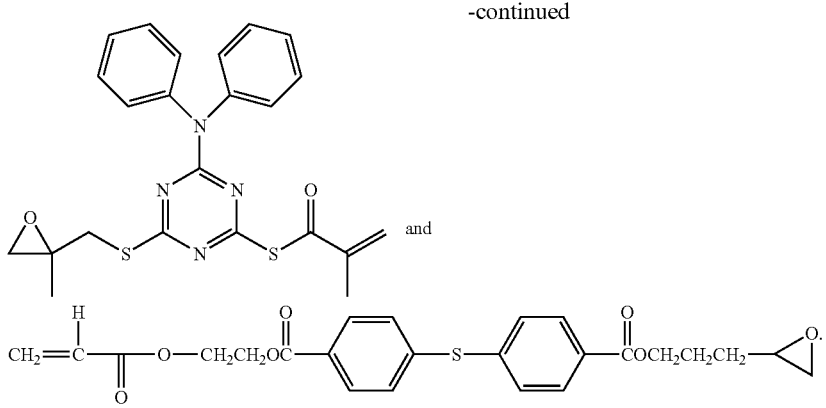

and

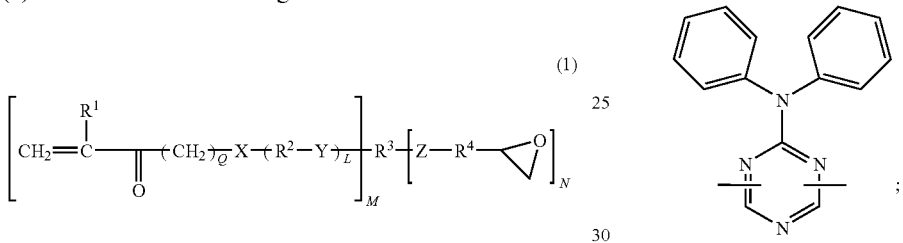

3. A photocurable composition comprising 1 to 99.99 weight % of a photopolymerizable monomer of the formula (1) below and 0.01 to 99 weight % of an initiator:

$$\left[ CH_2=\underset{R^1}{\overset{}{C}}-\underset{O}{\overset{}{C}}-(CH_2)_Q-X-(R^2-Y)_L \right]_M R^3 \left[ Z-R^4-\overset{O}{\triangle} \right]_N \tag{1}$$

wherein
R$^1$ is H or CH$_3$;
R$^2$ is C$_1$-C$_{20}$ alkylene;
R$^3$ is

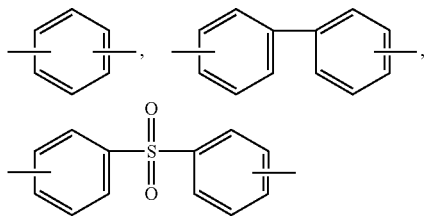

or

[structure: diphenylamino pyrazine]

;

R$^4$ is C$_1$-C$_{20}$ alkylene or C$_2$-C$_{20}$ alkyleneoxyalkyl;
X is O or S;
Y and Z are independently O, S, O—C=O or S—C=O;
L is 0 or an integer of 1 to 3;
M and N are independently an integer of 1 to 3; and
q is 0 or an integer of 1 to 30.

4. A photopolymer obtained by polymerizing the photocurable composition according to claim 3.

5. The photo polymer according to claim 4, which is used for optical functional materials or information processing devices.

* * * * *